(12) United States Patent
Horan et al.

(10) Patent No.: US 6,370,735 B1
(45) Date of Patent: Apr. 16, 2002

(54) SURGICAL LIGHT HANDLE

(76) Inventors: Robert T. Horan; Phyllis J. Horan, both of 11233 N. Pinto Dr., Fountain Hills, AZ (US) 85268

( * ) Notice: Subject to any disclaimer, the term of this patent is extended or adjusted under 35 U.S.C. 154(b) by 0 days.

(21) Appl. No.: 09/477,813

(22) Filed: Jan. 5, 2000

(51) Int. Cl.⁷ .............................. A45C 13/22; B25G 1/02
(52) U.S. Cl. ............................... 16/422; 16/906; 16/431
(58) Field of Search ........................ 16/422, 906, 421, 16/431, 436; 362/399, 400, 804

(56) References Cited

U.S. PATENT DOCUMENTS

| | | |
|---|---|---|
| 4,559,671 A | 12/1985 | Andrews et al. |
| 4,605,124 A | 8/1986 | Sandel et al. |
| D289,206 S | 4/1987 | Scoville, Jr. et al. |
| D298,864 S | 12/1988 | Jefferson |
| 4,844,252 A * | 7/1989 | Barron et al. ................. 16/421 |
| 4,974,288 A | 12/1990 | Reasner |
| 5,273,157 A | 12/1993 | Spina |
| 5,408,400 A * | 4/1995 | Gordon ....................... 16/421 |
| 5,493,757 A * | 2/1996 | Horan et al. .................. 16/422 |
| 5,604,955 A * | 2/1997 | Horan ........................ 362/399 |
| 5,697,123 A * | 12/1997 | Gharibian et al. ............ 16/422 |
| 5,709,465 A * | 1/1998 | Lanzone ..................... 362/399 |
| 5,735,598 A * | 4/1998 | Ramirez ...................... 16/422 |
| 5,884,996 A * | 3/1999 | Cottone et al. ............. 362/399 |

* cited by examiner

*Primary Examiner*—Chuck Y. Mah
(74) *Attorney, Agent, or Firm*—Lyon & Lyon LLP

(57) ABSTRACT

A sterile, disposable, plastic handle for use in manipulating a lamp above an operating table. The light handle has a threaded end upon which a flexible shield is threaded. The handle has a threaded end and a closed end. The handle and shield come fully assembled, and the shield is of such flexibility that it can be folded down around the handle during packaging as a way to save space and to prevent breaking or cracking of the shield. Two assembled handle and shield units are packaged together with the shields folded down.

15 Claims, 6 Drawing Sheets

SURGICAL LIGHT HANDLE

BACKGROUND OF THE INVENTION

1. Field of the Invention

This invention is in the field of hospital operating equipment, specifically, the overhead lighting used in hospital operating rooms. This invention is a novel form of handle for maneuvering an overhead lamp in the operating room.

2. Background

During surgery, it is necessary to provide overhead illumination above the operating table. Such illumination is provided by a lamp which is mounted above the operating table so that it can be manipulated to the height and/or position desired. To maneuver the light to the proper position, there is commonly provided a handle or grip with which the surgeon, nurses, or others on the operating team can move the lamp to the desired position. The lamp is generally mounted as to be moveable to any needed position, to permit vertical and lateral adjustment and to retain the lamp in any desired position until it is moved again to another position.

In some cases, the handle is a reusable metal part of the lamp. However, such a metal part requires sterilization of the handle before each operation. Disposable plastic handles are also in use in which a threaded upper portion can be screwed into a socket on the lamp structure or into an adapter which is secured to the lamp structure. Below the threaded portion is a handle which is gripped by hand. The handle is formed with a disc just beneath the threaded upper end which serves as a guard to prevent the sterile, gloved hand of the person manipulating the lamp from coming into contact with non-sterile parts of the lamp.

The disposable plastic handle is often preferred over a metal reusable handle because it can be packaged in a sterile container, removed from the sterile package at the time of use, and then discarded after the operation. Consequently, the hospital does not have to sterilize the handle.

The problems involved in previously available handles include bulkiness that causes storage problems and shields that either tear, crack, or break off during installation, assembly or use. The invention involved in this application addresses these problems by having a flexible shield that allows compact packaging and sterilization and which, because of its flexibility, resists cracking, tearing, and breaking.

SUMMARY OF THE INVENTION

The sterile handle and shield of this invention are designed to be detached from the operating room light upon completion of the operation and disposed of. The shield which attaches to the upper end of the plastic handle is designed to permit the shield to be folded such that it can be folded down in its assembled position in packaging and reduce the amount of space required for storing the invention. The assembled handle and shield are designed to be packaged together with two assembled handle and shield units in one package, which reduces storage space required for the invention and creates a convenient package that is ready to use in the operating room.

The shield is flexible and is designed to rebound back into its functional shape after being removed from the package. The flexibility and ability of the shield to rebound to its functional shape are significantly distinguishing factors of the invention from prior surgical lamp handles. The shield's flexibility allows it to be flexed without cracking, breaking, or losing its shape.

The shape of the shield may be conical, flat, or tapered such that the inside edges nearest the aperture are thinner than the outside edges. All of these characteristics give the handle and shield unit unique flexibility and functional significance.

DETAILED DESCRIPTION OF THE PREFERRED EMBODIMENTS

Figure 1:
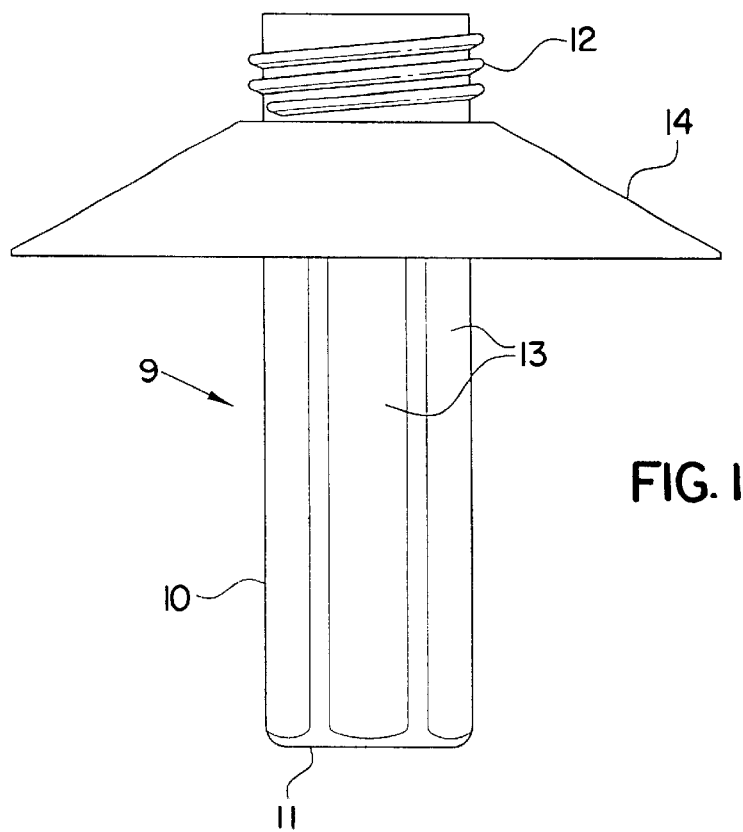
FIG. 1 is a side view of the handle and shield of the invention, with a conical-shaped shield sloping away from the threaded portion of the handle.

Referring now to the drawings and initially FIG. 1, the handle with a conical-shaped shield as a complete unit is indicated generally at 9. The handle 10, has a flat hexagonal base 11, and hexagonal sides 13.

Figure 2:
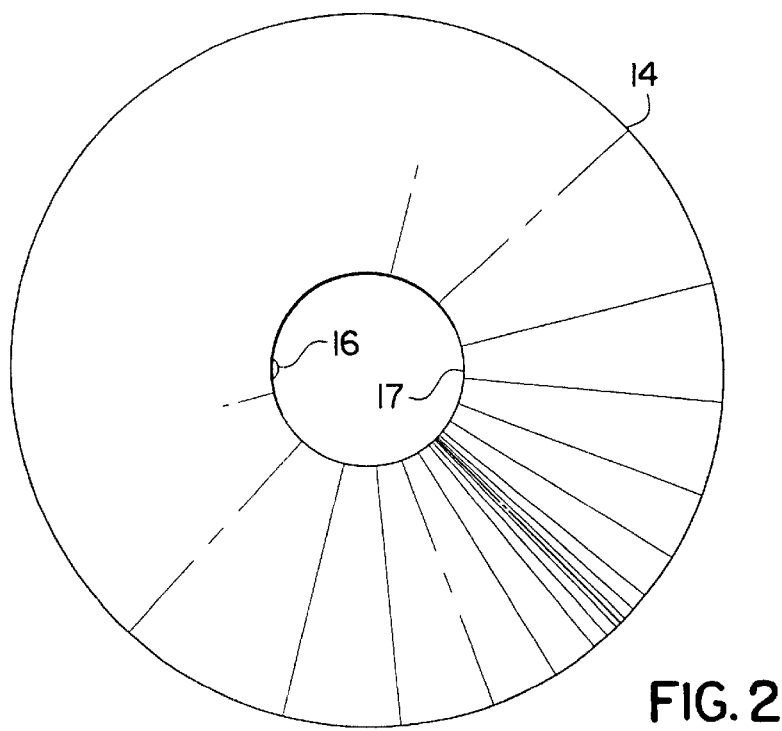
FIG. 2 is a top view of the shield, shown separately, which is designed for use with the handle of FIG. 1.

Referring to FIG. 2, the conical-shaped, flexible shield 14 has a tab 16 on the inside opening 17 of the shield to act as a guide for threading the shield onto the first thread of the handle.

Figure 3:
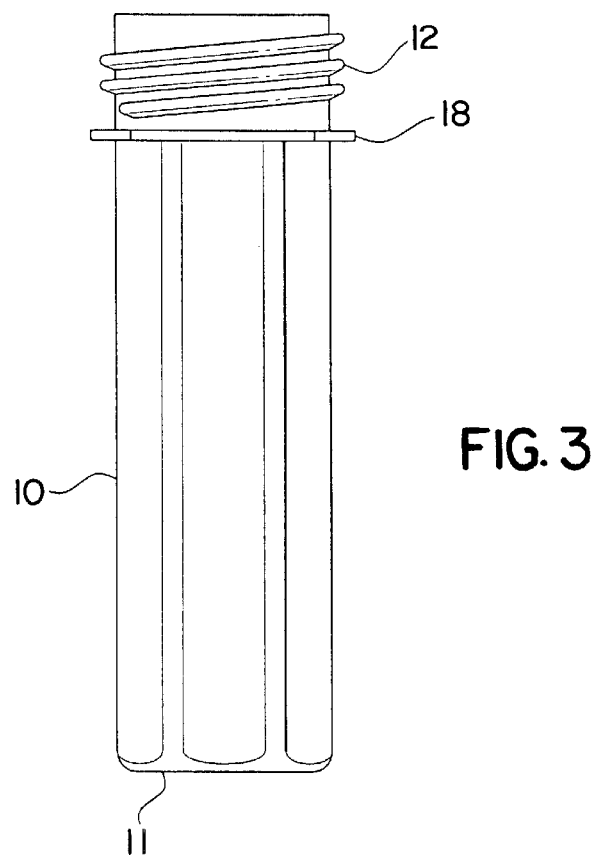
FIG. 3 is a side view of the handle without the shield.

Referring to FIG. 3, a threaded portion 12 at the top of the handle 10, is bounded by a shoulder or stop 18.

Figure 4:
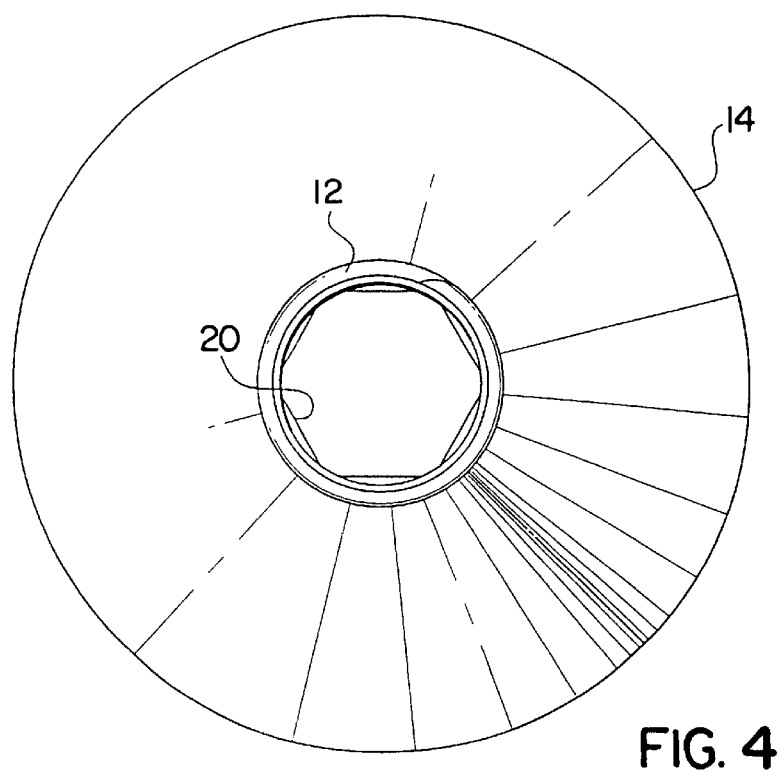
FIG. 4 is a top view of the handle and a conical-shaped shield.

Referring to FIG. 4, the inside of the handle portion is shown which has beveled edges 20 that correspond to the hexagonal sides.

Figure 5:
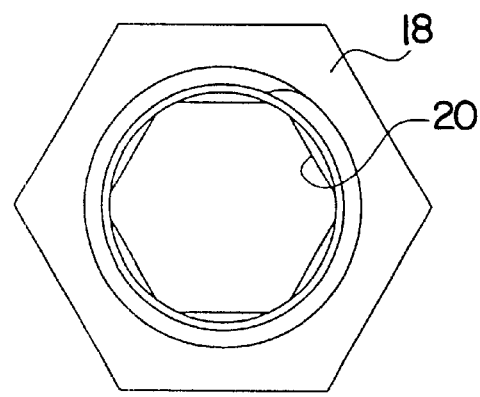
FIG. 5 is a top view of the handle and the shoulder of the handle.

Referring to FIG. 5, a top view of the handle 10 shows the shoulder 18 and the inside beveled edges 20 that correspond to the hexagonal sides.

Figure 6:
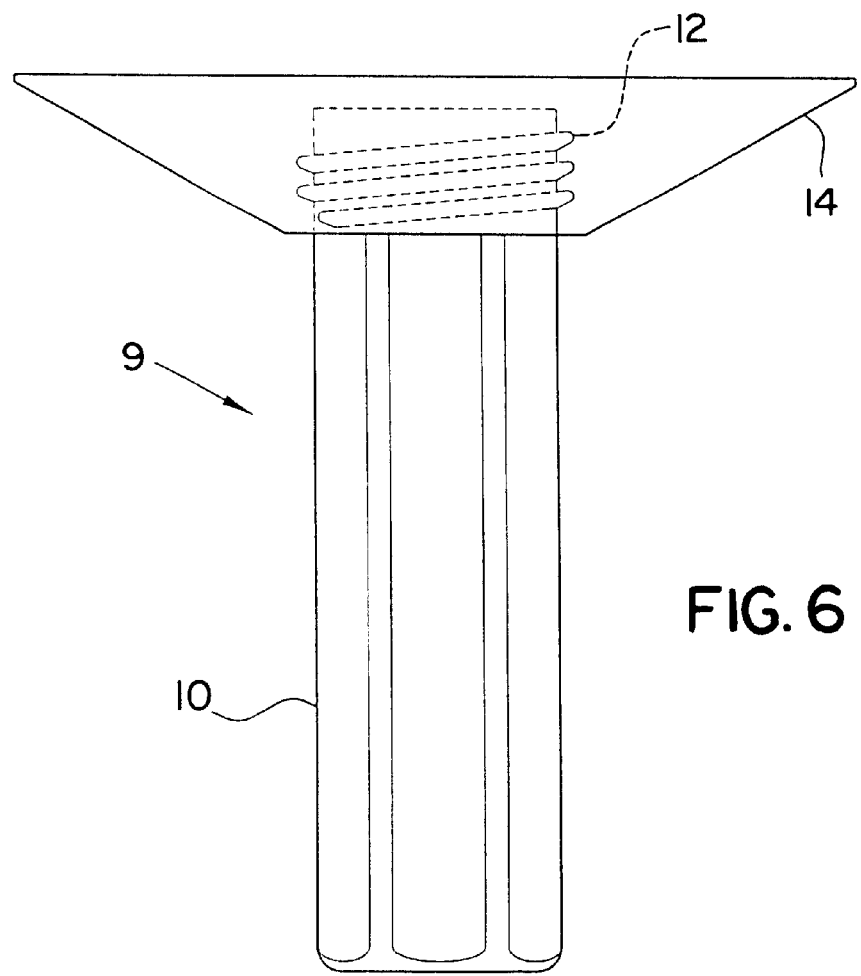
FIG. 6 is a side view of the handle and a conical-shaped shield sloping upwardly towards the threaded portion of the handle.

Referring to FIG. 6, the complete handle and shield assembly 9 is shown with a conical-shaped shield 14 inverted. Since the shield is made of a flexible material, it can be flipped into either the up or down position shown in FIGS. 1 and 6, as the user prefers.

Figure 7:
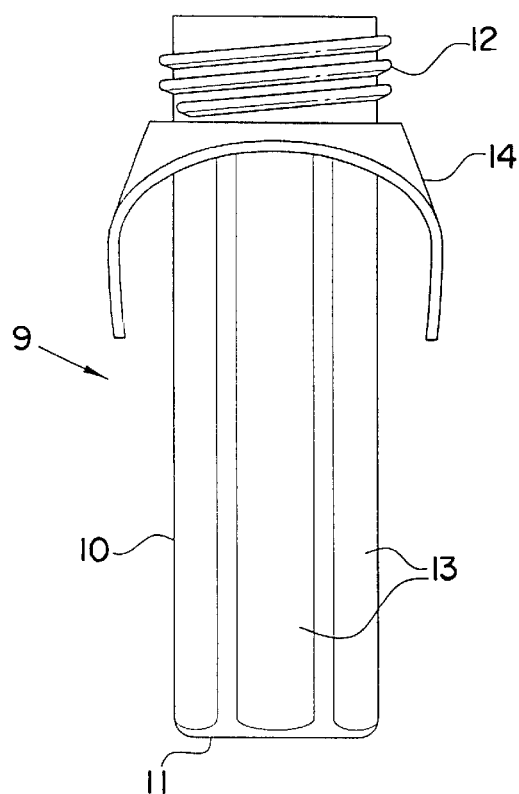
FIG. 7 is a side view of the handle with the shield folded down.

Referring to FIG. 7, the complete handle and shield assembly 9 is shown with the flexible shield 14 folded down toward the closed end 11 of the handle 10.

Figure 8:
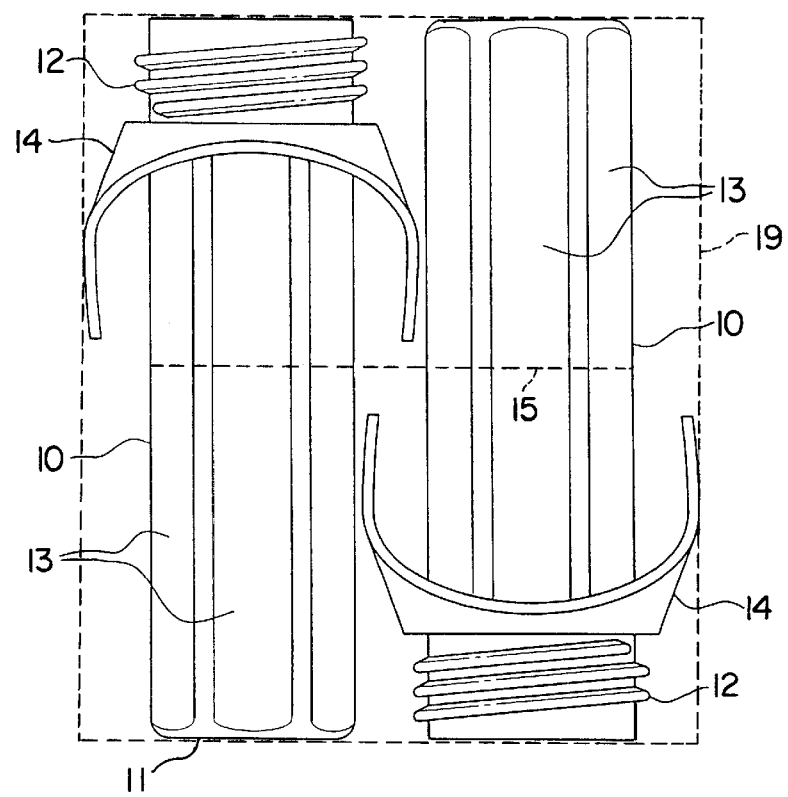
FIG. 8 is a side view of the handle and shield units shown in the manner they will be packaged.

Referring to FIG. 8, two complete handle and shield assemblies 9 are shown with the shields 14 being folded down. The two assembled units are placed side by side in a package 19 and are held together within the package by a band 15.

Figure 9:
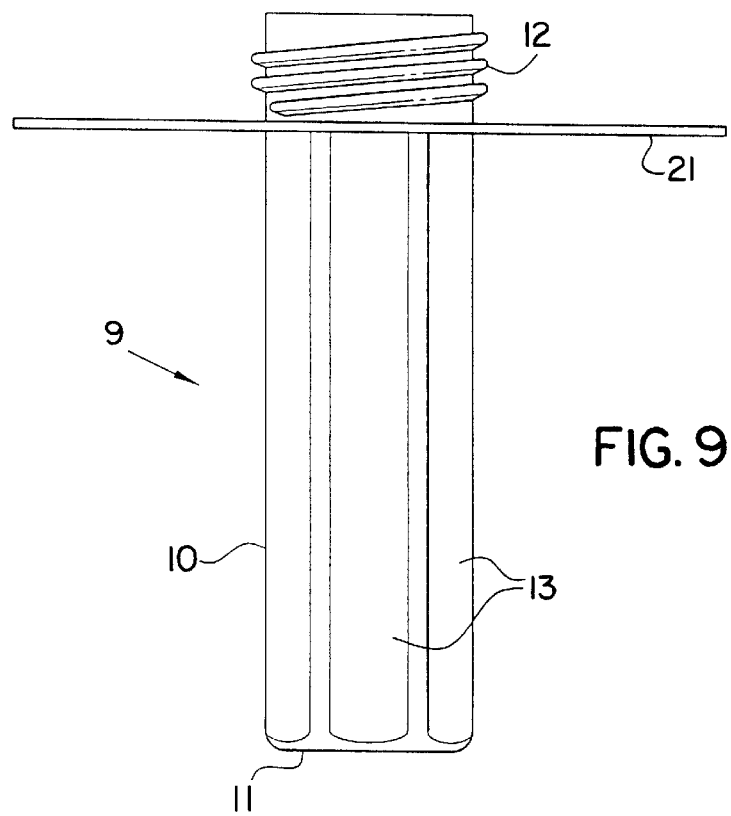
FIG. 9 is a side view of the handle with a flexible coplanar shield.

Referring to FIG. 9, the complete handle and shield assembly 9 is shown with a flexible, coplanar shield 21.

Figure 10:
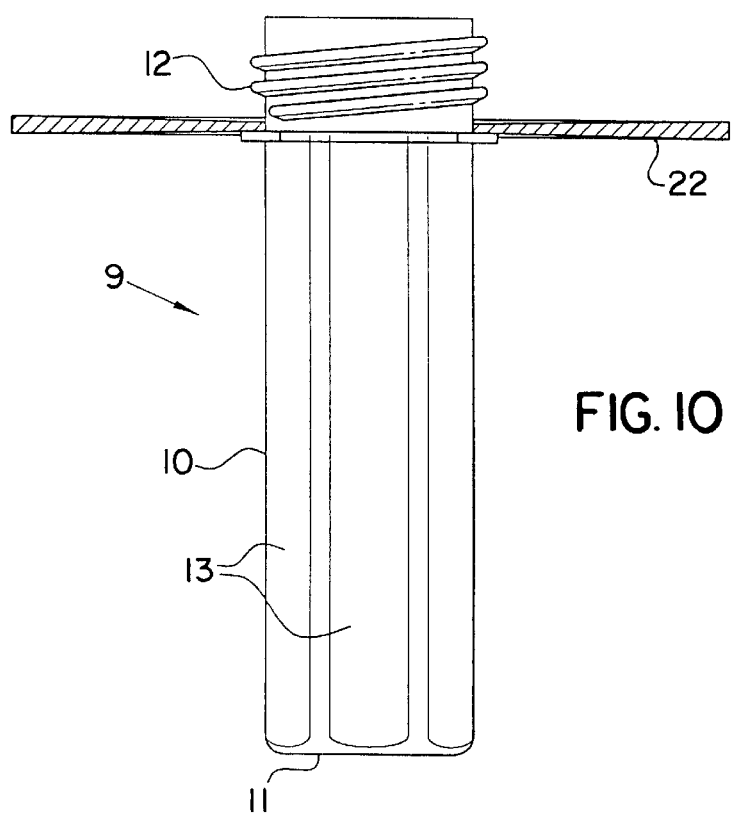
FIG. 10 is a side view of the handle with a flexible, tapered shield shown in cross section.

Referring to FIG. 10, the complete handle and shield assembly 9 is shown with a flexible, tapered shield shown in cross section that is thinner at the edge nearest the aperture and wider at the outer edge.

Dimensions of the handle 10 will be such that it can be conveniently grasped and manipulated by hand. The shields, either 14, 21 or 22, will have a diameter such that it will effectively prevent the manipulating hand or fingers from touching non-sterile surfaces when the handle is grasped.

The shield is preferably made of a blend of ultralinear low density polypropylene and ethyl vinyl acetate. The shield preferably is from about 0.020 to 0.040 inches thick. In the embodiment of FIG. 10, the shield preferably has a thickness of about 0.020 inches at the central opening, tapering up to about 0.040 inches thick at the perimeter.

Figure 11:
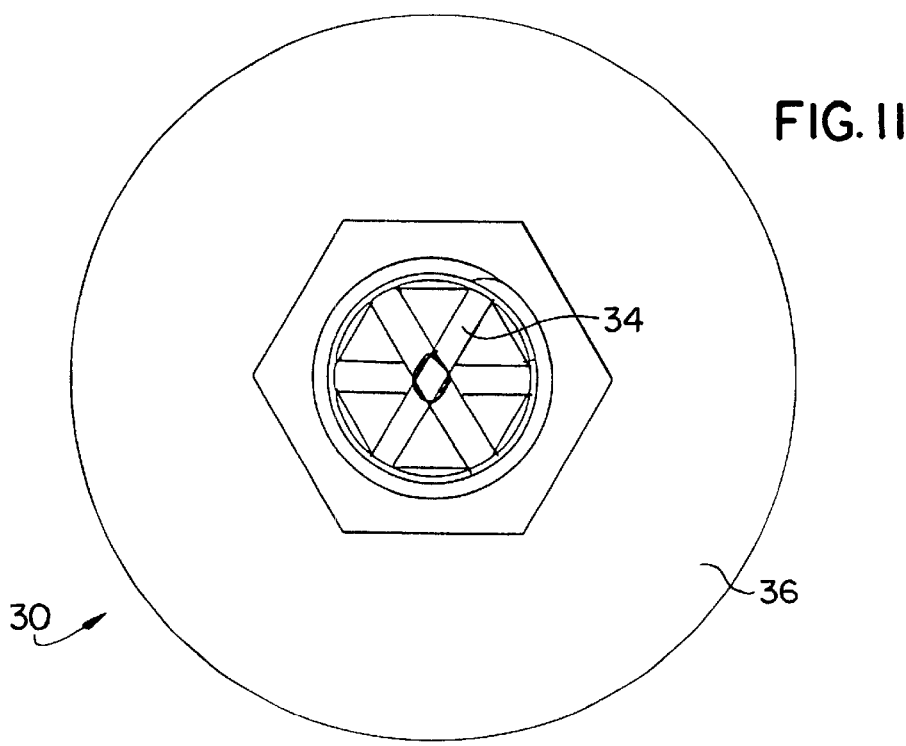
FIG. 11 is a top view of a single piece handle design.
Figure 12:
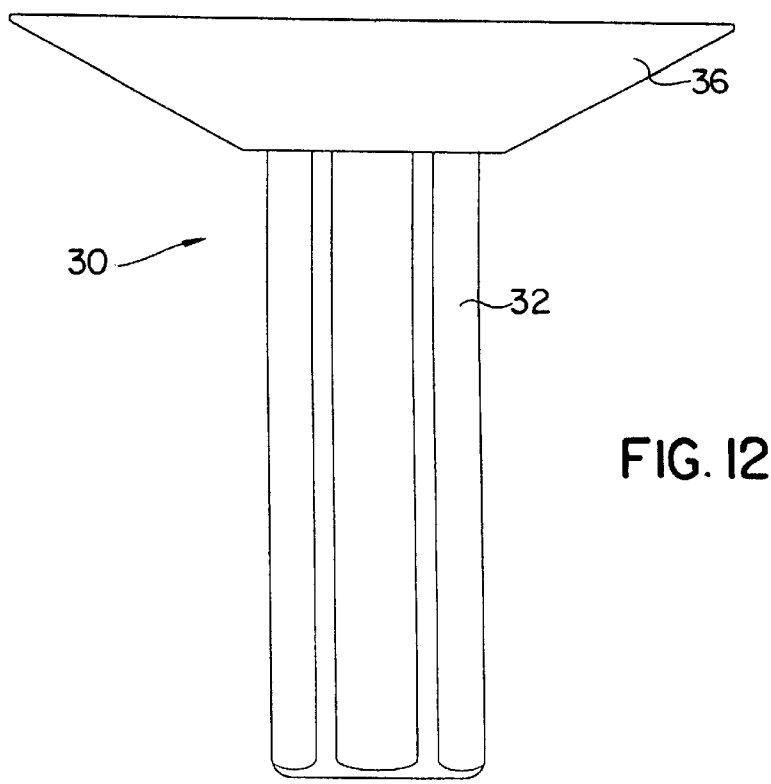
FIG. 12 is a side view thereof.

As shown in FIGS. 11 and 12, the light handle can be made as a single piece 30. The handle 32 is reinforced with cross bars 34 extending from the bottom to the top of the handle. This prevents the handle from flexing significantly, while allowing the disk section 36 to be folded flat against the handle 32 for packaging and storage. The single piece 30 is preferably a blend of ultralinear low density polypropylene and ethyl vinyl acetate.

Thus, a novel light handle has been shown and described. Various changes can of course be made without departing from the spirit of the invention. The invention, therefore, should not be restricted, except by the following claims and their equivalents.

What is claimed is:

1. A handle assembly for an operating room lamp, comprising:
    a handle having a threaded end and a closed end opposite the threaded end;
    a flexible shield having a central opening adapted to thread onto the threaded end of the handle, and with the flexible shield sufficiently flexible to allow any section of the shield to fold down alongside the handle when the handle and the flexible shield are fully assembled.

2. The handle assembly of claim 1 wherein the flexible shield is sufficiently flexible to allow the shield to return to a functional shape when the handle assembly is removed from a packaging.

3. The handle assembly of in claim 1 wherein the flexible shield comprises at least one of low density polypropylene and ethyl vinyl acetate.

4. The handle assembly set forth in claim 1 wherein the flexible shield is between 0.020 inches and 0.040 inches thick.

5. The handle assembly of claim 1 wherein the flexible shield is conically shaped.

6. The handle assembly of claim 1 wherein the flexible shield is flat.

7. The handle assembly of claim 1 wherein the flexible shield has a thickness greater at its perimeter than at the central opening.

8. The handle assembly set forth in claim 7 wherein an inner edge of the flexible shield that contacts the threaded end of the handle is approximately 0.020 inches thick, and an outer edge of the flexible shield is approximately 0.040 inches thick.

9. The handle assembly of in claim 1 wherein the handle includes cross bars to reduce flexing.

10. The handle assembly of claim 1 further comprising a shoulder integral with the handle and adjacent to the threaded end of the handle, with the shoulder contacting the flexible shield when the flexible shield is threaded onto the threaded end of the handle.

11. A handle assembly for an operating room lamp, comprising
    a handle having a threaded end and a closed end opposite the threaded end;
    a flexible shield on the handle, the flexible shield having a perimeter and a central opening with any section of the perimeter of the flexible shield moveable into a position alongside of the handle when the handle assembly is enclosed in a package.

12. The handle assembly of in claim 11 wherein the flexible shield is about 0.02–0.04 inches thick.

13. A package assembly, comprising
    a first handle assembly and a second handle assembly, each comprising
        a handle having a threaded end and a closed end opposite the threaded end;
        a flexible shield on the handle, the flexible shield having any pair of opposite sides foldable down alongside and substantially parallel to the handle regardless of the orientation of the handle and the flexible shield;
    a packaging around the first and second handle assemblies holding the flexible shields in folded down positions;
    wherein the closed end of the first handle is positioned adjacent to the threaded end of the second handle, and the closed end of the second handle is positioned adjacent to the threaded end of the first handle.

14. The package assembly of claim 13 further comprising a band around the first and second handle assemblies for holding the first and second handle assemblies together.

15. A handle unit for a lamp, comprising:
    a rigid handle having a first end and second end;
    screw threads on the first end;
    a shield on the handle, adjacent to the first end of the handle;
    with the shield comprising a flexible material, allowing any area of the shield to bend from a first position to a second position alongside of the handle, for packaging, and to bend back to the first position, during use of the handle unit on a lamp.

* * * * *